United States Patent [19]
Koop et al.

[11] Patent Number: 5,397,327
[45] Date of Patent: Mar. 14, 1995

[54] SURGICAL LASER HANDPIECE FOR SLIT INCISIONS

[75] Inventors: Dale E. Koop, Sunnyvale; Michael Arnett, Los Altos Hills, both of Calif.

[73] Assignee: Coherent, Inc., Santa Clara, Calif.

[21] Appl. No.: 98,879

[22] Filed: Jul. 27, 1993

[51] Int. Cl.⁶ .................. A61B 17/36; G02B 5/08
[52] U.S. Cl. .................. 606/17; 606/19; 606/18
[58] Field of Search .......... 606/17, 19, 15, 16, 606/9; 356/381, 382

[56] References Cited

U.S. PATENT DOCUMENTS

| | | | |
|---|---|---|---|
| 3,613,659 | 10/1971 | Phillips | 126/270 |
| 3,913,582 | 10/1975 | Sharon | 606/19 |
| 4,473,074 | 9/1984 | Vassiliadis | 606/19 |
| 4,484,334 | 11/1984 | Pressley | 372/101 |
| 4,518,232 | 5/1985 | Dagenais | 350/620 |
| 4,526,447 | 7/1985 | Taylor | 606/18 |
| 4,692,583 | 9/1987 | Kimura et al. | 219/121 L |
| 4,917,083 | 4/1990 | Harrington et al. | 606/15 |
| 5,080,474 | 1/1992 | Miyamoto | 350/433 |
| 5,138,490 | 8/1992 | Hohberg et al. | 359/570 |
| 5,139,494 | 8/1992 | Freiberg | 606/15 |
| 5,147,349 | 9/1992 | Johnson et al. | 606/4 |
| 5,148,326 | 9/1992 | Hohberg | 359/853 |
| 5,152,759 | 10/1992 | Parel et al. | 606/5 |
| 5,285,320 | 2/1994 | Hohberg | 359/853 |

FOREIGN PATENT DOCUMENTS 0296982 12/1988 European Pat. Off. ............ 606/4

OTHER PUBLICATIONS

K. D. Hanna, M.D., J. C. Chastang, L. Asfar, J. Samson, Y. Pouliquen, M.D., G. O. Warring III, M.D., "Scanning slit delivery system," *Journal of Cataract Refract Surgery*, vol. 15, Jul. 1989, pp. 390–396.

S. L. Ream, "A convex eam integrator," *Laser Focus*, Nov. 1979, pp. 68, 70–71.

*Primary Examiner*—Stephen C. Pellegrino
*Assistant Examiner*—Sonya C. Harris
*Attorney, Agent, or Firm*—Limbach & Limbach

[57] ABSTRACT

A slit incision handpiece that receives a circular laser beam, reshapes the beam to have an elliptical cross-section, and focuses the beam onto target tissue. Slit incisions of approximately the dimensions of the elliptical beam are formed by stationary exposures on the target tissue from the output of the slit incision handpiece.

9 Claims, 8 Drawing Sheets

SURGICAL LASER HANDPIECE FOR SLIT INCISIONS

FIELD OF THE INVENTION

This invention relates to medical lasers wherein a laser beam is focused into a narrow ellipse and used to ablate slit shaped incisions in tissue.

BACKGROUND OF THE INVENTION

Historically, surgical incisions in tissue have been performed with sharp metal cutting instruments. More recently, lasers have become the tool of choice in many medical procedures to cut and treat tissue. Laser beams can be accurately focused on tissue to cut many desired shapes and depths. The slit incision, a very narrow elongated incision, is especially appropriate for laser surgery. Surgeons can make these narrow incisions by passing a focused laser beam over the target tissue.

One medical procedure where slit incisions are desired is hair transplants. Hair transplants have become a common cosmetic procedure, particularly for the treatment of male pattern baldness. In a hair transplant procedure, a piece of the patient's skin having healthy growing hair is removed from a donor region on the scalp and implanted into a hairless, recipient region. This process involves cutting a hole or slit into the recipient region so that the new plug of hair can be inserted. Slit grafting is modernly used because of its many cosmetic and medical advantages over circular punching.

Historically, slit grafting has been accomplished by cutting a slit into the recipient region with a scalpel. More recently, lasers have been used. A laser is more advantageous because the size and shape of the incision can be more accurately controlled. A laser beam, usually a pulsed infrared beam, is focused onto the scalp. The exposure can be controlled to remove the amount of skin needed for the hair graft dimensions. Another advantage of using lasers to cut or remove skin is the coagulating effects of the laser light that minimizes bleeding and pain. Further, the laser radiation removes the skin in the slit it creates thereby creating room for the new plug of hair to be placed inside. This eliminates the compression problems involved with inserting a plug of hair in a narrow slit created with a scalpel. The use of lasers for hair transplants is further discussed in the applicant's co-pending application, "Laser Assisted Hair Transplant Method", Application Ser. No. 08/012,895, filed Feb. 3, 1993.

A laser beam can be accurately focused on the scalp by a variety of optical delivery systems. One such system is marketed by the assignee in conjunction with its sealed carbon dioxide medical laser system under the name Ultrapulse 5000. The Ultrapulse system includes an articulated arm to direct the laser beam to its intended target. This articulated arm is composed of multiple successive straight segments connected by rotatable joints. In each joint there is an optic or a set of optics. A laser beam enters the first segment of the articulated arm toward the first joint. The beam is redirected by the optic(s) in that joint down the center of the next segment. The beam continues down successive segments being redirected at each joint. The beam is directed to its intended target through the last segment by the last optic in the last joint of the articulated arm. All the joints can rotate while maintaining beam alignment down the successive segment. Therefore, the user can direct the beam using the last segment of the arm to any target location in any angle desired.

To create a slit using the articulated arm, the surgeon positions the output segment of the articulated arm so that the beam will impinge on the target tissue. The surgeon then presses a footswitch which opens a shutter that allows light to exit the delivery end of the articulated arm. The doctor then moves the delivery end over the target tissue until the desired slit width and depth is created.

The drawback to this or most other optical delivery systems is that it takes time and skill to create a slit or series of slits of the desired dimensions. The doctor must time the exposure and the speed of movement of the arm to remove the proper amount of skin in the scalp while ensuring the slit is consistent throughout its length. Since the number of slits required can be as numerous as the number of individual hair follicles being transplanted, the time and skill required to create accurate slits in the recipient area can be great.

There is a need for an optical delivery system that creates a slit of proper dimensions with as little as one single stationary exposure.

One method of achieving this goal is to impinge an elliptically shaped beam on the target tissue. In the prior art, elliptical beam profiles have been used to cut slit incisions in eyes. In this prior system, discussed in U.S. Pat. No. 5,152,759, the beam was transformed from a round beam to an elliptical beam by the use of a slit mask. More specifically, a beam having a circular cross-section is passed through a slit. The portion of the beam transmitted through the slit will have an elliptical cross-section. The drawback of this method is that it is inefficient. Laser power is wasted because much of laser beam is blocked by the slit mask to create the resulting elliptically shaped beam. While the loss of laser power may not have been significant for applications in eye surgery, tissue ablation requires higher power beams and therefore the use of a slit mask would not be suitable.

Another drawback of slit masks is that light which is not transmitted through the slit must be either reflected or absorbed by the mask creating further complications.

There is a need for an optical delivery system that creates an elliptical beam without any significant loss of laser power in the delivery and beam shaping system.

SUMMARY OF THE INVENTION

These problems have been overcome by the present invention. In the preferred embodiment, a slit incision handpiece is attached to the end of the articulated arm. This slit incision handpiece has beam shaping optics that reshape a circular laser beam into a narrow ellipse. The shape of this ellipse is such that the doctor need make as little as one exposure with the elliptical laser beam and a slit of the desired dimensions is created on the scalp. This process does not require the doctor to move the handpiece during the exposure to create the slit, so it is faster and requires less surgical skill.

In another preferred embodiment, the beam shaping optics are incorporated in one of the joints of the articulated arm. The beam shaping optics would not only reshape the beam into an ellipse, but also serve to redirect the beam down the center of the following segment of the articulated arm.

The advantages of the present invention are that the doctor can create an accurate slit with less surgical skill.

The doctor can also perform this step more quickly and without moving the arm manually.

Another advantage over the prior art is the use of optics to form the elliptical beam. By using optics instead of a slit mask, no laser energy is wasted when the laser beam shape is transformed to an ellipse.

DETAILED DESCRIPTION OF THE INVENTION

Figure 1:
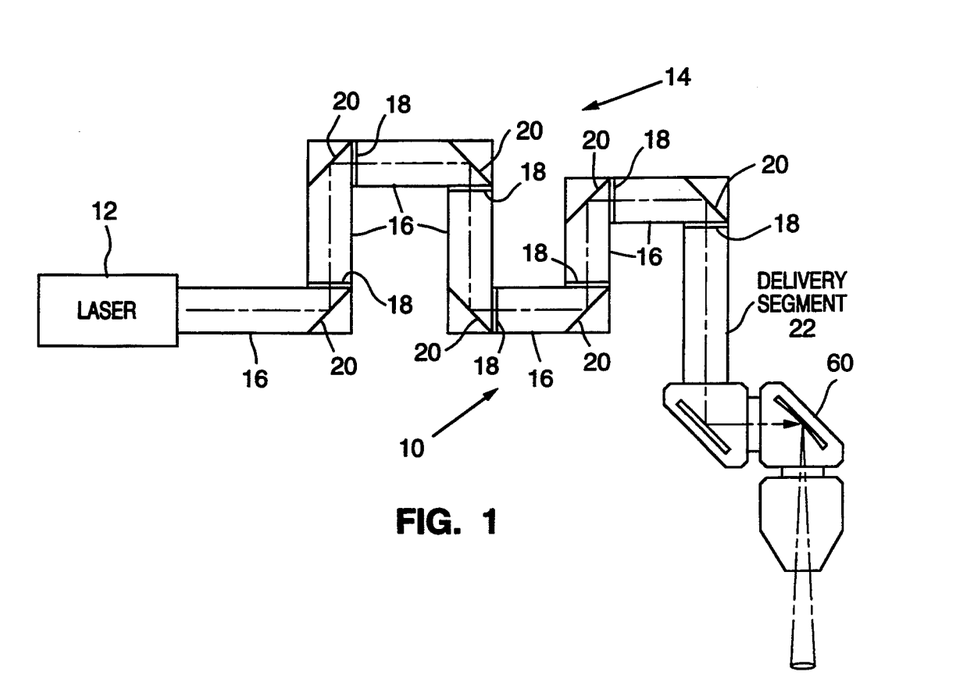
FIG. 1 is a schematic view of a surgical laser system. An articulated arm is attached to the output of a laser. A laser incision handpiece is attached to the output end of the articulated arm.

Referring to FIG. 1, a surgical laser system used to create slit incisions is designated in its entirety by the number 10. The surgical laser system 10 includes a laser module 12 that produces a laser beam with a substantially circular cross-section. The most common lasers used for high power tissue ablation are Carbon Dioxide lasers. These lasers can be pulsed or continuous wave. The preferred embodiment uses a laser manufactured by the assignee under the name Ultrapulse 5000, which will be discussed later.

The output of the laser system 12 is directed into an articulated arm 14 which is composed of multiple successive straight segments 16 connected end to end by rotatable joints 18. For each rotatable joint 18, there is an associated mirror 20. A laser beam entering each segment 16 of the articulated arm 14 is redirected down the subsequent segment 16 by the mirror 20 associated with each rotatable joint 18. All the rotatable joints 18 rotate while maintaining beam alignment down the successive segment 16 so that delivery segment 22 can direct the beam to any target location in any angle desired. The delivery segment 22 directs the beam out of the articulated arm either to the target tissue or another delivery system. The embodiment in FIG. 1 shows the delivery segment 22 directing the beam into a three section slit incision handpiece 60. This embodiment of the slit incision handpiece 60 will be discussed later with reference to FIG. 5.

Figure 2:
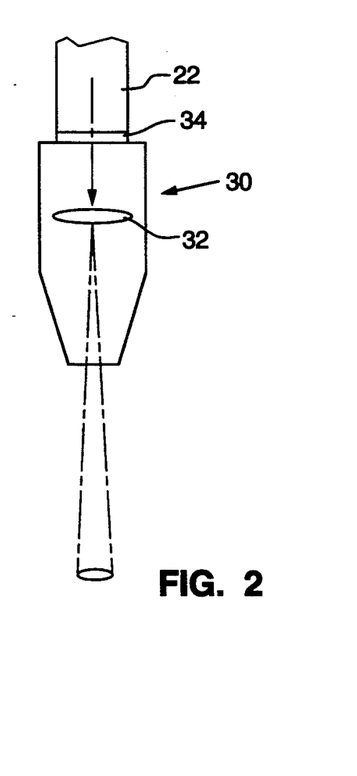
FIG. 2 is a schematic view of a single section slit incision handpiece embodiment that contains a lens.

The embodiment shown in FIG. 2 illustrates the subject invention in a basic form having a single section slit incision handpiece designated in its entirety by the number 30. The handpiece 30 can be attached to the delivery segment 22 of the articulated arm 14 by a swivel joint 34. An astigmatic focusing lens 32 is mounted inside the handpiece 30 and functions to change the circular beam to an elliptical beam having the desired dimensions at the point the beam reaches the target tissue. The handpiece 30 can be rotated about the swivel joint 34 so as to attain the desired slit orientation on the target tissue.

Figure 2B:
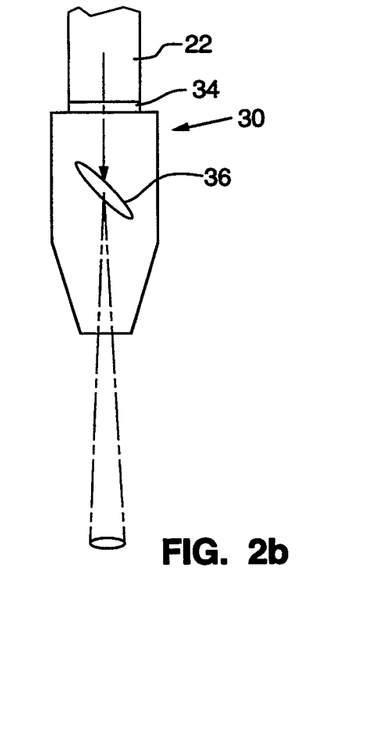

The embodiment in FIG. 2b shows a single section slit incision handpiece 30 whereby the optical element in the handpiece 30 is a cylindrical or spherical focusing lens 36. The beam shaping is accomplished by placing the focusing lens 36 in the handpiece at an angle to the beam (not at normal incidence). In this orientation, the focusing lens 36 has a stronger focusing effect in one plane than the other.

Figure 3:
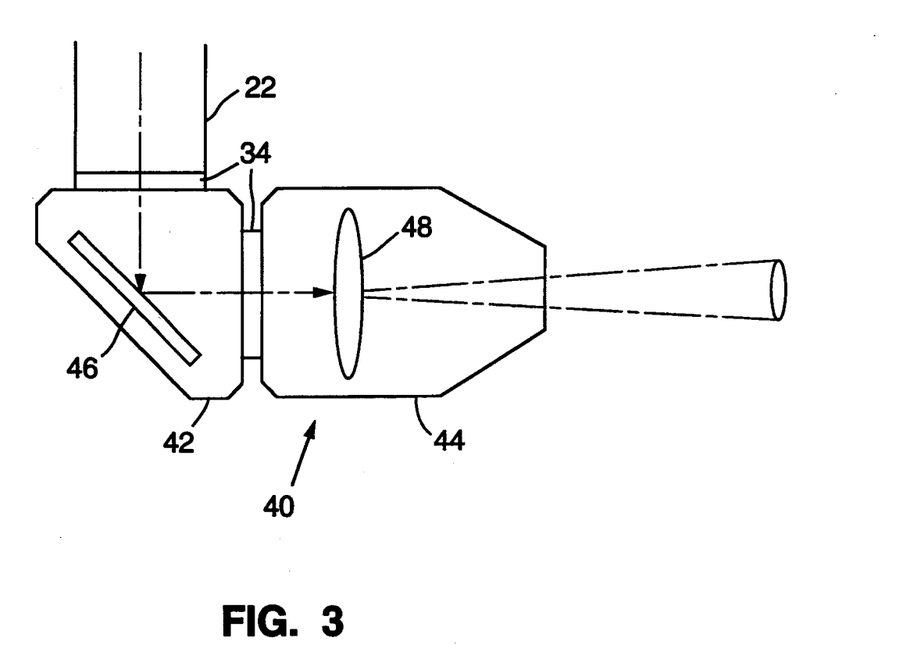
FIG. 3 is a schematic view of a double section slit incision handpiece. The first section contains a mirror and the delivery end contains an astigmatic focusing lens to reshape the beam.

The embodiment in FIG. 3 shows a two section slit incision handpiece designated in its entirety by the number 40. The handpiece 40 includes a first section 42 and a delivery section 44. The first section 42 is attached to the delivery segment 22 of the articulated arm 14 by a swivel joint 34, and the delivery section 44 is attached to the first section 42 by a swivel joint 34.

The sections 42 and 44 can accommodate optics that direct, focus and reshape the beam as it passes through the two section handpiece 40.

The embodiment in FIG. 3 shows a two section slit incision handpiece 40 where a mirror 46 is mounted in the first section 42 so as to direct the laser beam into the delivery section 44. An astigmatic focusing lens 48 is mounted inside the delivery section 44 so as to change the circular beam to an elliptical beam having the desired dimensions when the beam reaches the target tissue.

Figure 4:
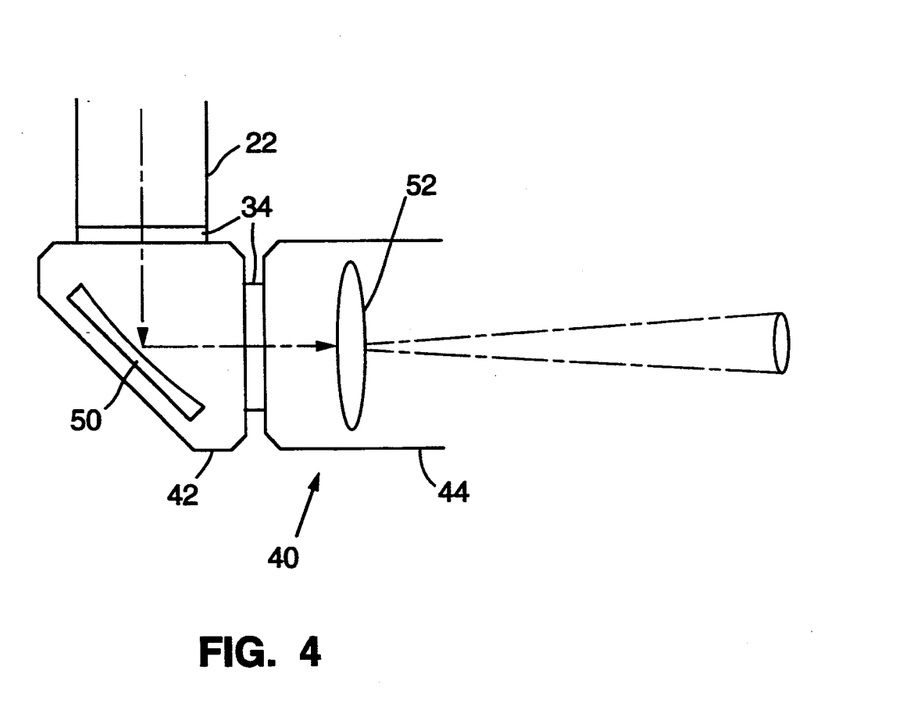
FIG. 4 is a schematic view of a slit incision handpiece that has a first section and an output section. The first section contains a beam shaping mirror and the output section contains a lens.

The embodiment shown in FIG. 4 is the same as in FIG. 3 except the mirror 50 in the first section 42 is a beam shaping mirror 50, and the lens in the delivery section 44 is a standard focusing lens 52. The beam shaping mirror 50 is mounted in the first section 42 so as to simultaneously reshape the laser beam to an ellipse and direct it to the delivery section 44. The beam shaping mirror 50 can be spherical, ellipsoidal or cylindrical. The focusing lens 52 focuses the beam so that it has the desired dimensions when the beam reaches the target tissue. In addition, the beam shaping mirror 50 can have a curvature such that it both reshapes the beam and focuses the beam to have the desired dimensions when it reaches the target tissue. If so, then the focusing lens 52 can be eliminated from the embodiment of FIG. 4.

Figure 5:
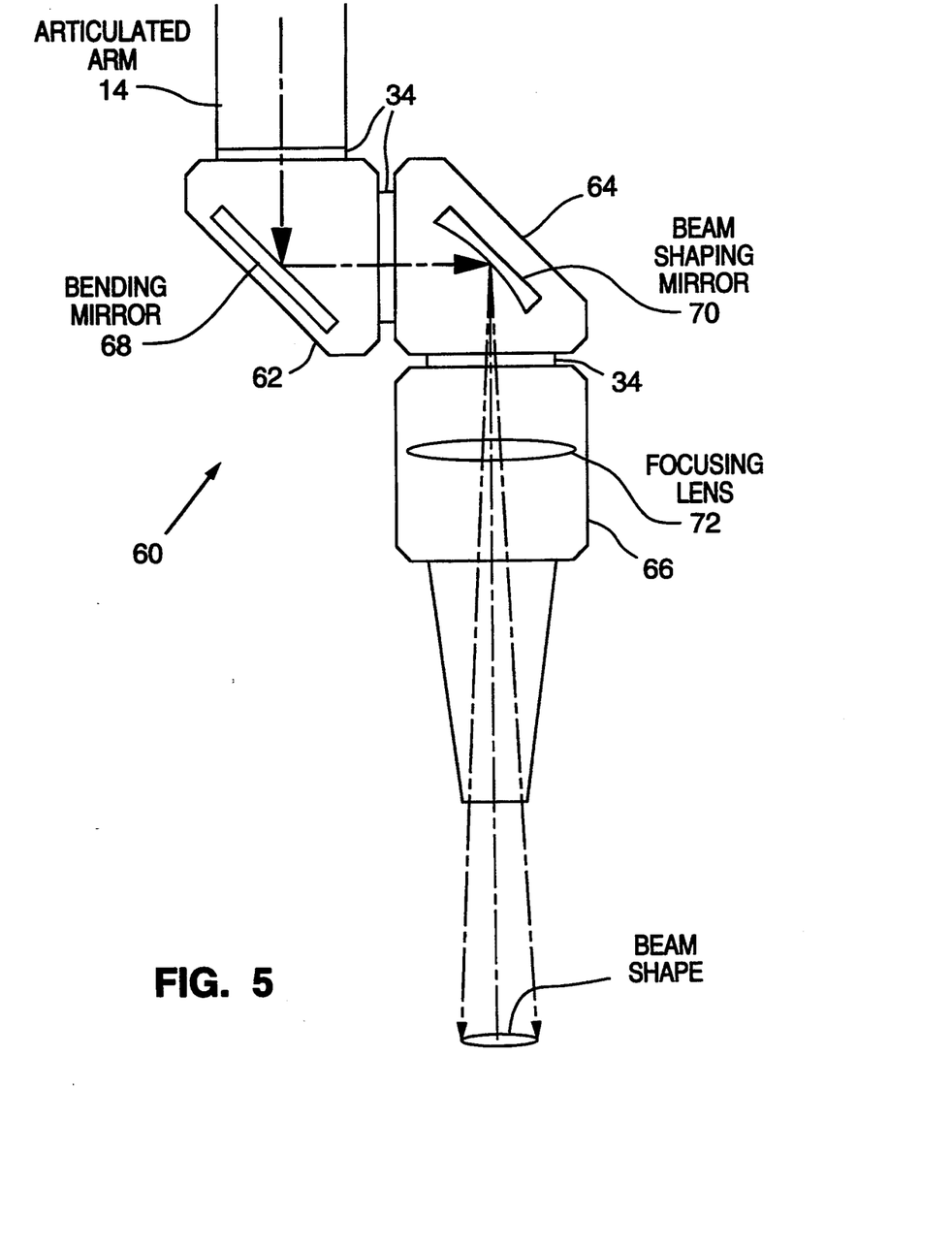
FIG. 5 is a schematic view of a slit incision handpiece that has a first, middle and output section. The first section contains a bending mirror, the middle section contains a beam shaping mirror and the output section contains a focusing lens.

The embodiment shown in FIG. 5 is a three section slit incision handpiece designated in its entirety by the number 60. The handpiece 60 has a first section 62, a middle section 64, and a delivery section 66. The middle section 64 is attached to the first section 62 and the delivery section 66 by swivel joints 34 so that each section can rotate relative to another. The first section 62 is also attached to the delivery segment 22 of the articulated arm 14 by a swivel joint 34.

Each section 62, 64, and 66 can accommodate optics that direct, focus, and reshape the beam as it passes through the three section handpiece 60.

The embodiment in FIG. 5 shows a three section slit incision handpiece 60 where a mirror 68 is mounted in the first section 62 so as to redirect a beam entering the first section 62 into the middle section 64. Inside the middle section 64, a beam shaping mirror 70 is mounted so as to simultaneously reshape the laser beam to an ellipse and direct it to the delivery section 66. The beam shaping mirror 70 can be spherical, ellipsoidal or cylindrical. The reshaped beam then passes a focusing lens 72 mounted in the delivery section 66 so as to focus the beam to the desired dimensions when the beam reaches the target tissue.

Figure 6:
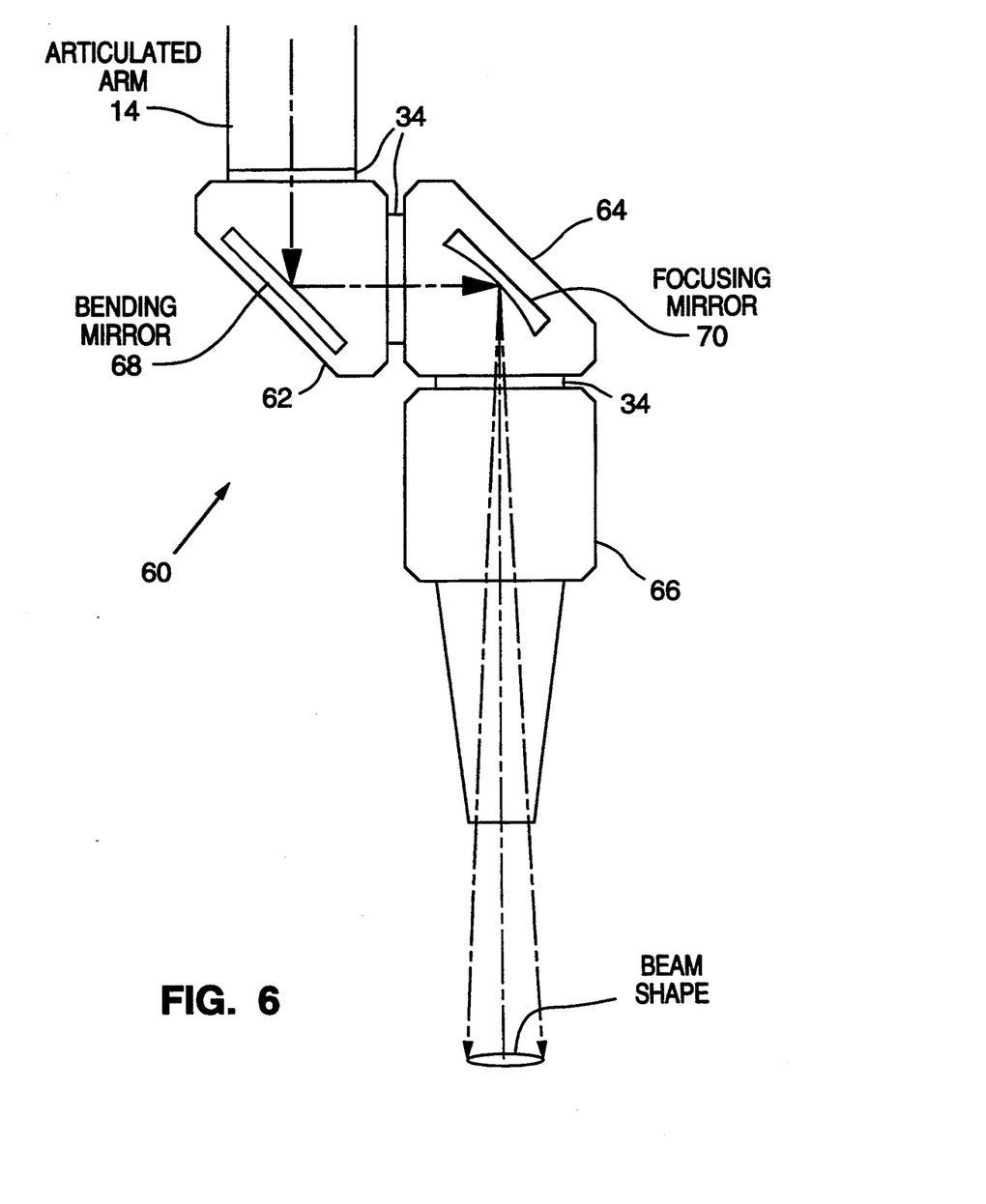
FIG. 6 is a schematic view of a slit incision handpiece that has a first, middle and output section. The first section contains a bending mirror, the middle section contains a beam shaping mirror and the output section contains no optics.

The embodiment shown in FIG. 6 is the same as in FIG. 5 except there is no focusing lens in the delivery section 66. Instead, the beam shaping mirror 70 has a curvature such that it both reshapes the beam and focuses the beam so that the beam has the desired dimensions when it reaches the target tissue.

Figure 7:
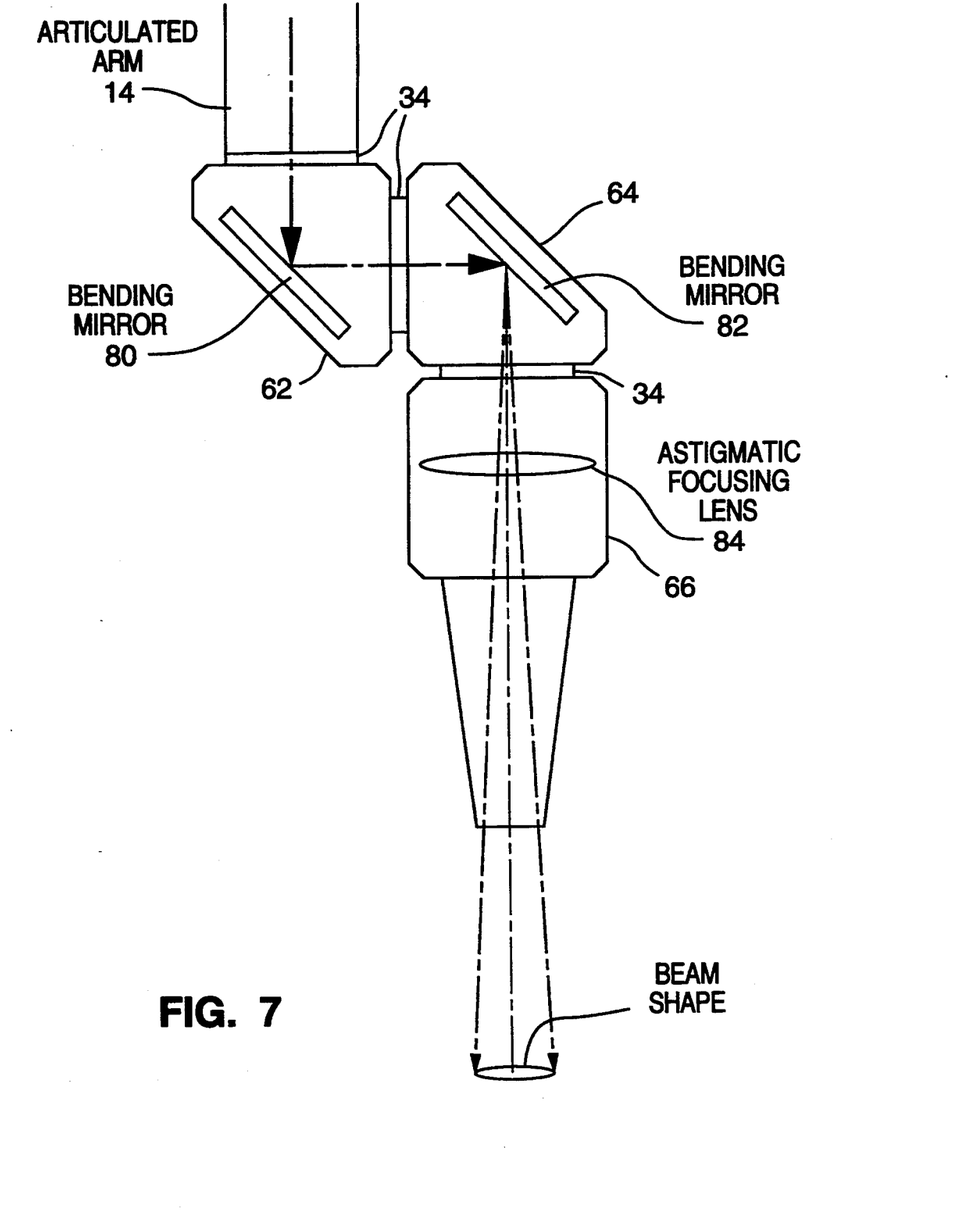
FIG. 7 is a schematic view of a slit incision handpiece that has a first, middle and output section. The first and middle sections contain beam bending mirrors and the output section contains an astigmatic focusing lens.

The embodiment shown in FIG. 7 is the same as in FIG. 5 except that the mirror in the middle section 64 is a flat turning mirror 82 and the lens in the delivery section 66 is an astigmatic focusing lens 84. The directing mirror inside the middle section 64, is mounted so as to redirect a beam entering the middle section 64 into the delivery section 66. The astigmatic focusing lens 84 is mounted inside the delivery section 66 so as to simultaneously reshape the laser beam to a narrow ellipse and focus the beam onto the target tissue such that the beam has the desired dimensions when the beam reaches the target tissue. The delivery section 66 can be rotated about the swivel joint 34 that attaches the delivery section 66 to the middle section 64 so as to attain the desired slit orientation on the target tissue.

While the embodiments shown in FIGS. 1-7 illustrate the slit incision handpieces 30, 40, and 60 that are attached to the delivery segment 22 of the articulated arm 14, the slit incision handpieces 30, 40, and 60 can be attached to the output of any optical delivery system or laser system so as to reshape a circular beam and focus it onto the target tissue with the desired elliptical dimensions.

Figure 8:
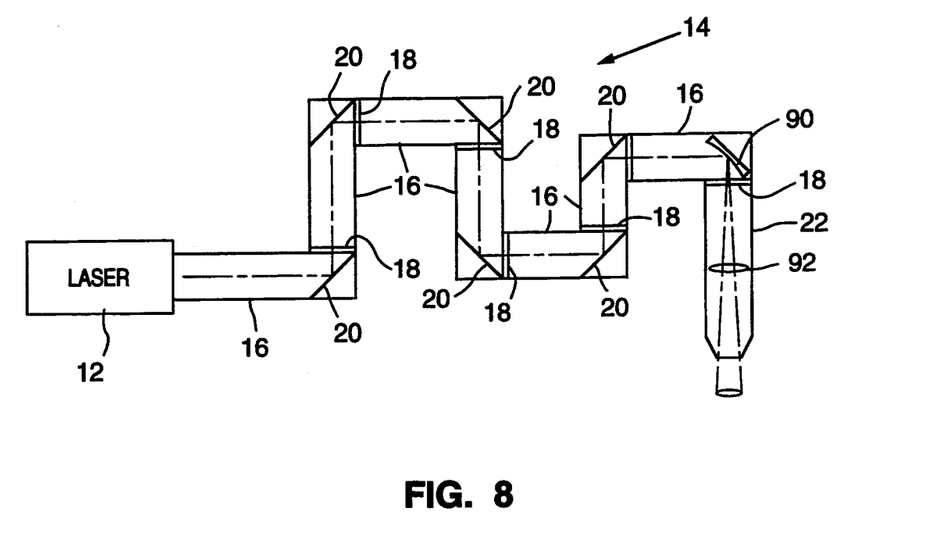
FIG. 8 is a schematic view of an articulated arm whereby the slit incision handpiece optics have been incorporated into the optics of the articulated arm.

The slit incision handpiece optics can also be incorporated into the articulated arm 14. The embodiment in FIG. 8 shows a beam shaping mirror 90 mounted in the last rotatable joint 18 of the articulated arm 14. The beam shaping mirror 90 serves to redirect the laser beam to the target tissue through the output section 22 and to reshape the beam from a circular cross-section to an elliptical cross-section. The beam shaping mirror 90 can be spherical, ellipsoidal or cylindrical and could be mounted in any of the rotatable joints 18 of the articulated arm 14. A focusing lens 92 is mounted in the delivery section 22 so as to focus the beam so that the beam has the desired dimensions when the beam reaches the target tissue. In addition, the beam shaping mirror 90 can have a curvature such that it both reshapes the beam and focuses the beam to have the desired elliptical dimensions when it reaches the target tissue. If so, then the focusing lens 92 is not needed and is not present in the delivery segment 22.

Figure 9:
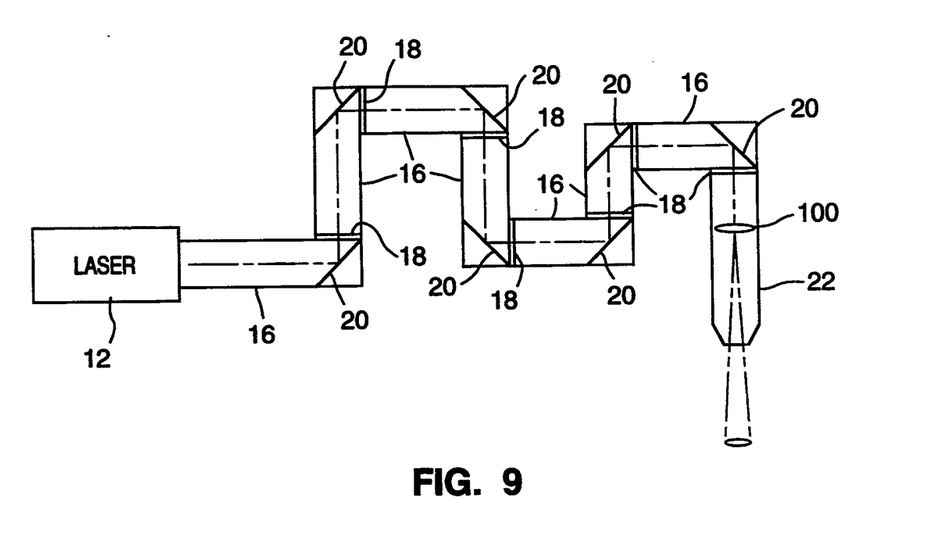
FIG. 9 is a schematic view of an articulated arm whereby the slit incision handpiece optics have been incorporated into the optics of the articulated arm.

The embodiment shown in FIG. 9 is the same as in FIG. 8 except that last mirror in the articulated arm 14 is a flat reflecting mirror, and the lens in the delivery section 22 is an astigmatic focusing lens 100. The astigmatic focusing lens 100 reshapes the beam so that it has the desired dimensions when the beam reaches the target tissue. The delivery segment 22 can be rotated about the rotatable joint 18 so as to attain the desired slit orientation on the target tissue.

The surgical laser system 10 is capable of creating slit incisions in tissue without moving the beam during the exposure. When an elliptical beam impinges the target tissue, the tissue is ablated so as to create a slit having approximately the same shape as the beam. The dimensions of the slit will depend on the power and shape of the beam, and the exposure time.

The power of the beam will be determined by the laser system used. In the preferred embodiment, the laser beam is created by the Ultrapulse 5000, a carbon dioxide laser manufactured and sold by the assignee. The Ultrapulse 5000 produces a pulsed infrared laser beam having maximum specifications of 500 mj per pulse, a pulse duration of up to 1 ms, at a repetition rate of 500 Hz, for an average power of 250 Watts.

The output beam entering the articulated arm has a circular cross-section. The shape of the beam as it reaches the target tissue is dictated by the optics used in the slit incision handpiece 30, 40, or 60.

One medical procedure where slit incisions are desired is hair transplants. For this procedure, the desired dimensions for a slit incision in the recipient region on the scalp are approximately 0.5 mm wide, 4.5 mm long, and 4 to 5 mm deep. For the surgical laser system 10 to produce the desired slit in a single exposure, the Ultrapulse 5000 laser system can be set to produce 250 mj pulses at a repetition rate of 40 Hz to produce 10 watts of average power. The optics in the slit incision handpiece 30, 40, or 60 are designed to produce a beam having approximately the same dimensions as the desired slit when the beam reaches the tissue. An exposure time of approximately 1 second will produce a slit incision on the scalp having the desired dimensions and depth.

The design of the optics necessary to produce the desired beam dimensions will vary depending on the configuration of optical elements used and the characteristics of the laser beam as it enters the handpiece.

Figure 10:
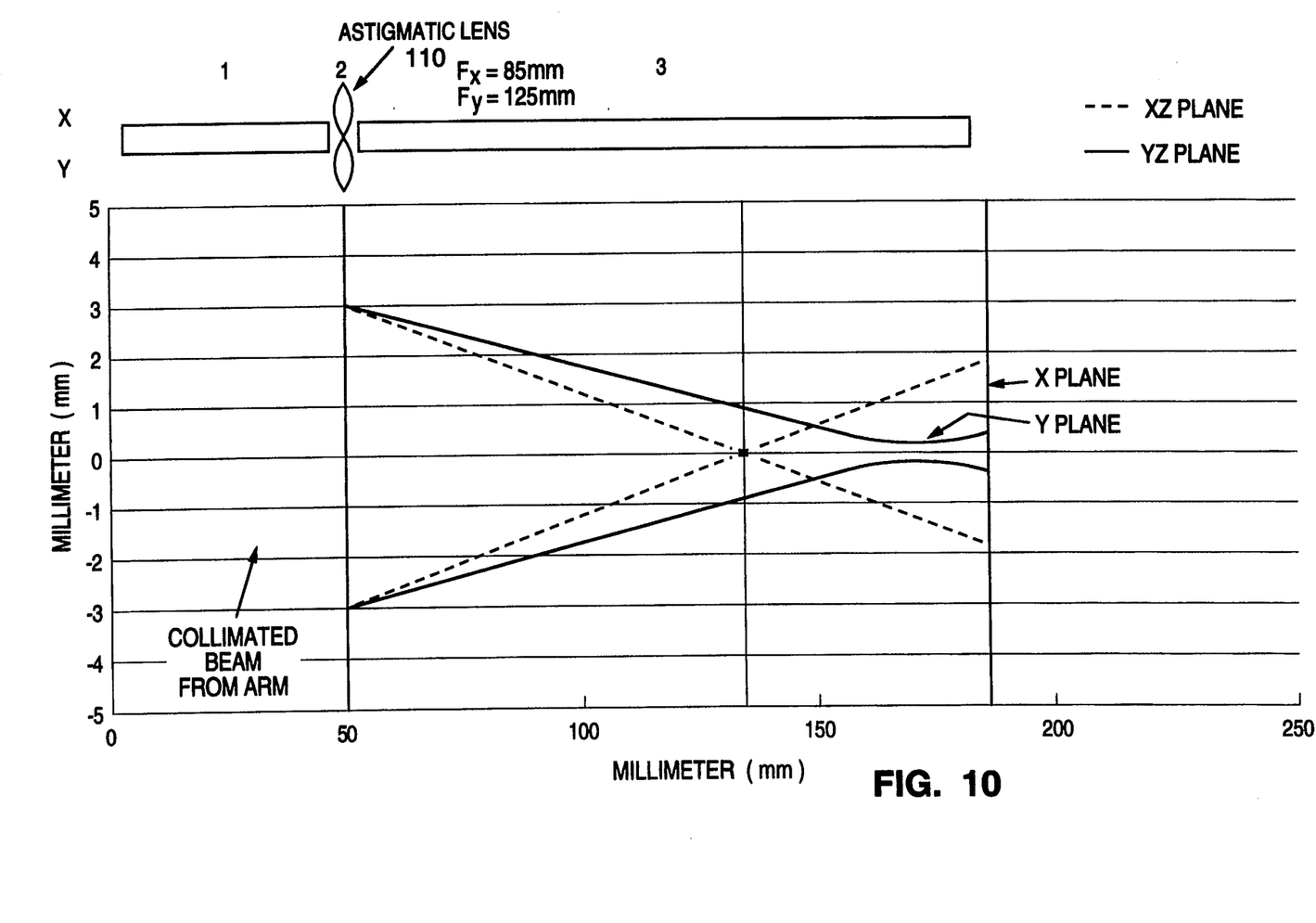
FIG. 10 is a graphical drawing showing the beam diameter in both the X and Y planes as a function of distance for a slit incision handpiece that uses an astigmatic lens.
Figure 11:
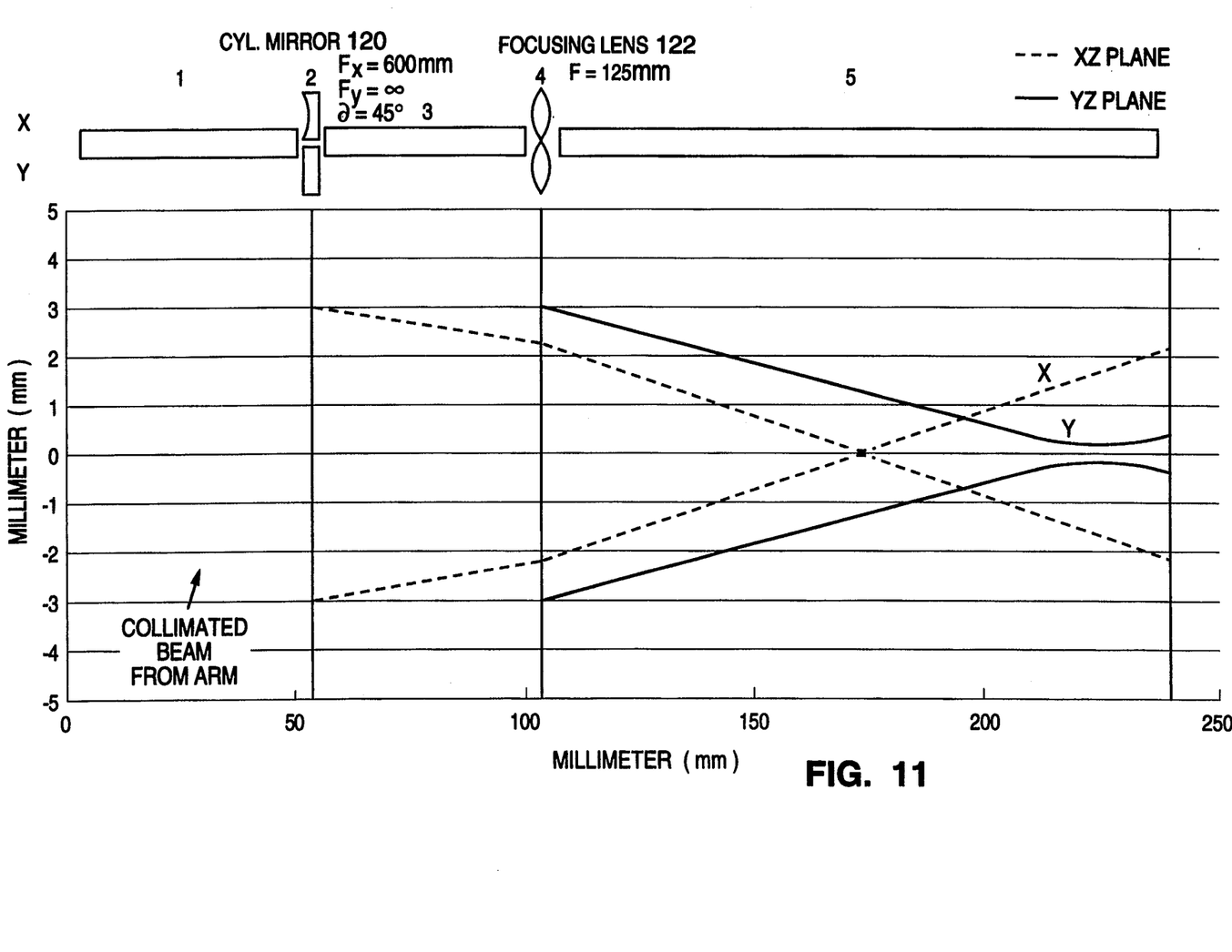
FIG. 11 is a graphical drawing showing the beam diameter in both the X and Y planes as a function of distance for a slit incision handpiece that uses a cylindrical mirror and a focusing lens.

FIGS. 10 and 11 illustrate examples of optical elements suitable for performing slit incisions with a laser for hair transplant surgery. FIG. 10 illustrates the use of an astigmatic lens of the type shown in FIGS. 2, 3, 7, or 9. For this embodiment, it is assumed that the laser produces a beam at 10.6 $\mu$m having a diameter of 6 mm as it exits the articulated arm 14. An astigmatic lens 110 having a focal length of 85 mm in the X plane and a focal length of 125 mm in the Y plane will produce a beam having the desired dimensions at a distance of approximately 130 mm from the lens 110.

FIG. 11 illustrates the use of a beam shaping mirror in conjunction with a focusing lens as shown in FIGS. 4, 5, or 8. A cylindrical beam shaping mirror 120 is oriented at an angle of 45 degrees having a focal length of 600 mm in the X plane and a focal length of $\infty$ in the Y plane. The cylindrical mirror 120 is used in conjunction with a focusing lens 122 having a focal length of 125 mm. At a distance of 50 mm apart, the cylindrical mirror 120 and the focusing lens 122 produce a beam having the desired dimensions at a distance of approximately 130 mm from the focusing lens 122.

We claim:

1. A surgical handpiece incorporated into an articulated arm for connection to a laser generating a beam having a substantially circular cross-section, and delivering the beam to a target tissue to create a slit incision, comprising:

an articulated arm having straight segments connected end to end by rotatable joints;

an optic in each of the joints whereby the laser beam traveling down each of the segments is redirected down the subsequent segment; and at least one of the optics in one of the joints being a beam shaping mirror that changes the shape of the beam in a manner so that the beam has an elliptical cross-section when the beam reaches the target tissue.

2. A surgical handpiece for connection to a laser that generates a beam having a substantially circular cross-section, said handpiece for delivering the beam to a target tissue to create a slit incision, the handpiece comprising:

conduit means having a central channel for transmitting the laser beam; and optical means within the channel for changing the shape of the beam in a manner so that the beam has an elliptical cross-section when the beam reaches the target tissue whereby an elongated strip of tissue can be ablated.

3. A surgical handpiece as recited in claim 2 wherein the optical means is a beam shaping mirror.

4. A surgical handpiece as recited in claim 2 wherein the optical means is a beam shaping mirror and a lens.

5. A surgical handpiece as recited in claim 2 wherein the optical means is a lens.

6. A surgical handpiece as recited in claim 2 whereby the handpiece is attached to an articulated arm.

7. A surgical handpiece as recited in claim 2 wherein the conduit means further includes a first section and a second section connected together by a swivel joint;

the conduit means further including a pair of mirrors disposed therein, with one of the mirrors defining the optical means for changing the shape of the beam;

the first section containing one of the mirrors; and the second section containing the other mirror.

8. A surgical handpiece as recited in claim 2 further comprising:

the conduit means having a first section, a middle section and a second section;

the first section and the middle section being connected together by a swivel joint;

the middle section and the second section being connected together by a second swivel joint; and two optical elements disposed inside the conduit means, one of which defining the optical means for changing the shape of the beam.

9. A surgical handpiece as recited in claim 8 wherein the two optical elements are defined by a lens and a mirror; and the optical means for changing the shape of the beam are defined by both the lens and the mirror.

* * * * *